（12）United States Patent
Lisanti et al.

(10) Patent No.: US 11,964,983 B2
(45) Date of Patent: Apr. 23, 2024

(54) SELECTIVE CDK4/6 INHIBITOR CANCER THERAPEUTICS

(71) Applicant: LUNELLA BIOTECH, INC., Ottawa (CA)

(72) Inventors: Michael P. Lisanti, Didsbury Village Greater Manchester (GB); Federica Sotgia, Didsbury Village Greater Manchester (GB); Jussi Kangasmetsa, Cambridge (GB)

(73) Assignee: LUNELLA BIOTECH, INC., Ontario (CA)

( * ) Notice: Subject to any disclaimer, the term of this patent is extended or adjusted under 35 U.S.C. 154(b) by 0 days.

(21) Appl. No.: 18/008,636

(22) PCT Filed: Jun. 10, 2021

(86) PCT No.: PCT/IB2021/055124
§ 371 (c)(1),
(2) Date: Dec. 6, 2022

(87) PCT Pub. No.: WO2021/250614
PCT Pub. Date: Dec. 16, 2021

(65) Prior Publication Data
US 2023/0227461 A1 Jul. 20, 2023

Related U.S. Application Data

(60) Provisional application No. 63/037,898, filed on Jun. 11, 2020.

(51) Int. Cl.
*C07D 487/14* (2006.01)
*C07D 487/20* (2006.01)

(52) U.S. Cl.
CPC ......... *C07D 487/14* (2013.01); *C07D 487/20* (2013.01)

(58) Field of Classification Search
CPC .............................. C07D 487/14; C07D 487/20
See application file for complete search history.

(56) References Cited

U.S. PATENT DOCUMENTS

2014/0275066 A1 9/2014 Sharpless et al.

FOREIGN PATENT DOCUMENTS

WO  WO-2018005863 A1 * 1/2018 .............. A61P 25/02
WO  2018/106870       6/2018

OTHER PUBLICATIONS

Golub et al. Science, vol. 286, Oct. 15, 1999, pp. 531-537.*
International Search Report and Written Opinion of the ISA dated Aug. 30, 2021, for PCT/IB2021/055124, 12 pp.

* cited by examiner

*Primary Examiner* — Samira J Jean-Louis
(74) *Attorney, Agent, or Firm* — Nixon & Vanderhye, P.C.

(57) ABSTRACT

This disclosure describes embodiments of selective and potent CDK 4/6 inhibitors that show advantageous inhibition of cancer growth, even at low concentrations. As described herein, compounds of the present approach comprise substituted pyridinylpiperazine-pyrrolopyrimidine compounds having a fatty acid moiety. The compounds described herein may be used as pharmaceutical compounds for anti-cancer therapies, and are useful for the treatment, prevention and/or amelioration of cancer. Formula (a)

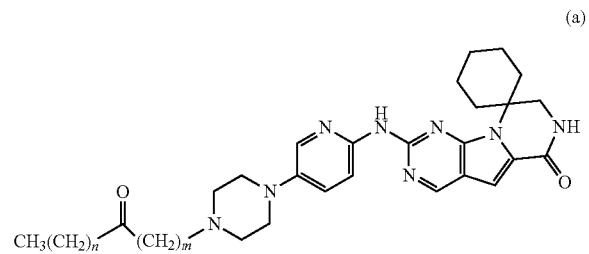

5 Claims, No Drawings

SELECTIVE CDK4/6 INHIBITOR CANCER THERAPEUTICS

CROSS-REFERENCE TO RELATED APPLICATION(S)

This application is the U.S. national phase of International Application No. PCT/IB2021/055124 filed Jun. 10, 2021, which designated the U.S. and claims the benefit of U.S. provisional application No. 63/037,898 filed Jun. 11, 2020, the entire contents of each of which are hereby incorporated by reference.

FIELD

The present disclosure relates to pharmaceutical compounds for anti-cancer therapies, and more specifically to substituted pyridinylpiperazine-pyrrolopyrimidine compounds, that are potent CDK 4/6 inhibitors and also may be used for the treatment, prevention, and/or amelioration of cancer.

BACKGROUND

Cancer stem cells (CSCs) are tumor-initiating cells (TICs) that are resistant to conventional cancer therapies, such as chemo-therapy and radiation treatment. As a consequence, CSCs are responsible for both tumor recurrence and distant metastasis, driving treatment failure and poor clinical outcomes in cancer patients. Therefore, innovative approaches are necessary to understand how to tackle the problem of CSCs. Mechanistically, this may be related to the ability of CSCs to survive and thrive under harsh conditions and different micro-environments. Because CSCs are an especially small sub-set of the tumor cell population, their metabolic and phenotypic properties have remained largely uncharacterized, until recently.

Moreover, CSCs are strikingly resilient and highly resistant to cellular stress, which allows them to undergo anchorage-independent growth, especially under conditions of low-attachment. As a consequence, they form 3D spheroids, which retain the properties of CSCs and stem cell progenitors. In contrast, when subjected to growth in suspension, most "bulk" cancer cells die, via anoikis—a specialized type of apoptosis. As such, the clonal propagation of a single CSC results in the production of a 3D spheroid and does not involve the self-aggregation of cancer cells. Therefore, 3D spheroid formation is a functional read-out for stemness in epithelial cancer cells and allows one to enrich for a population of epithelioid cells with a stem-like phenotype. These 3D spheroids are also known as mammospheres when they are prepared using breast cancer cells, such as MCF7, among others.

Previously, 3D spheroids have been generated from 2 distinct ER(+) cells lines (MCF7 and T47D) and subjected to unbiased label-free proteomics analysis. This work started the analysis of the phenotypic behavior of CSCs at a molecular level. The 3D spheroids were directly compared with monolayers of these cell lines and processed in parallel. This allowed for an identification of the proteomic features that are characteristic of the CSC phenotype in 3D spheroids, relative to monolayers. Based on this molecular analysis, mammospheres were observed to be significantly enriched in mitochondrial proteins. These mitochondrial-related proteins included molecules involved in beta-oxidation and ketone metabolism/re-utilization, mitochondrial biogenesis, electron transport, ADP/ATP exchange/transport, CoQ synthesis and ROS production, as well as the suppression of mitophagy. As such, increased mitochondrial protein synthesis or decreased mitophagy could allow the accumulation of mitochondrial mass in CSCs.

Given the increases in CSCs, mitochondrial mass is being considered as a new metabolic biomarker to purify CSCs. Using this overall approach, it has been observed that it was possible to significantly enrich CSC activity using only MitoTracker, as a single marker for both ER(+) (MCF7) and ER(−) (MDA-MB-231) breast cancer cell lines. Remarkably, MitoTracker-high cells were found to be chemo-resistant to Paclitaxel, exhibiting resistance to the Paclitaxel-induced DNA-damage response.

What is needed, however, are new pharmaceutical compounds for anti-cancer therapies that eradicate CSCs, prevent or reduce the likelihood of metastasis and/or recurrence, and reduce or eliminate cancer resistance to chemotherapies and other anti-cancer therapies. Additionally, what is needed are therapeutic strategies and anti-cancer therapies that specifically target the "fittest" CSCs, and eliminate further cancer growth, including anchorage-independent growth, tumor recurrence, and distant metastasis.

BRIEF SUMMARY

Cancer stem cells (CSCs) are now believed to be one of the main root causes of treatment failure in cancer patients world-wide. Mechanistically, this may be related to the ability of CSCs to survive and thrive under harsh conditions and different micro-environments. The inventors proposed the theory that CSCs might become resistant to conventional therapies by "boosting" ATP production using an elevated mitochondrial OXPHOS metabolism. Consistent with this view, a variety of mitochondrial inhibitors successfully blocked 3D tumor sphere formation, including i) FDA-approved antibiotics (doxycycline, tigecycline, azithromycin, pyrvinium pamoate, atovaquone, bedaquiline), ii) natural compounds (actinonin, CAPE, berberine, brutieridin and melitidin), as well as iii) experimental compounds (oligomycin and AR-C155858, an MCT1/2 inhibitor), among others.

Cyclin-dependent kinases (CDKs) 4 and 6 are enzymes known to promote cell mitosis and meiosis, both in normal cells and in cancer cells. These enzymes are responsible for phosphorylating and thus deactivating the retinoblastoma protein, which plays a role in cell cycle progression from the G1 phase to the S phase. Research has identified abnormalities in cancer cells that increase the activity of CDKs. This increased activity results in an inactivation of various tumor suppressor genes, and thus paves the way for rapid cancer stem cell proliferation and tumor growth. Naturally occurring protein inhibitors of CDKs, such as p16 and p27, have been shown to inhibit growth in vitro of lung cancer cell lines. Certain CDK inhibitors may be useful as chemoprotective agents through their ability to inhibit cell cycle progression of normal untransformed cells.

Targeted inhibition of these enzymes is one potential strategy for anti-cancer treatments and therapeutics, either alone or in combination with other therapies. Blocking the CDK 4/6 pathway prevents cells from progressing to the S phase, which effectuates cell death via apoptosis. Described herein are embodiments of pyrrollopyrimidine compounds that are CDK inhibitors, and primarily inhibitors of CDK 4 and CDK 6 ("CDK 4/6"), that have strong efficacy as cancer therapeutics. More specifically, embodiments of anti-cancer CDK 4/6 inhibitors according to the present approach are substituted pyridinylpiperazine-pyrrolopyrimidine compounds having a fatty acid moiety. The compound shown below, in which 'm' is an integer from 0-4, and more preferably 0-2, and 'n' is an integer from 13-22, and more preferably from 12-20, is illustrative of some embodiments in the first class of anti-cancer CDK 4/6 inhibitors.

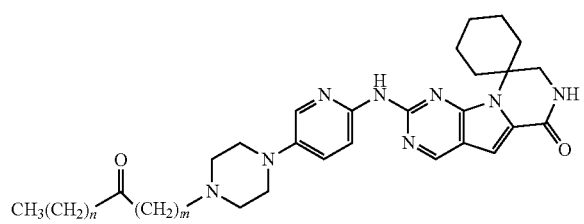

The compound below, in which 'm' is 0 and 'n' is 13, is an illustrative embodiment of the pyridinylpiperazine-pyrrolopyrimidine anti-cancer CDK 4/6 inhibitors described herein.

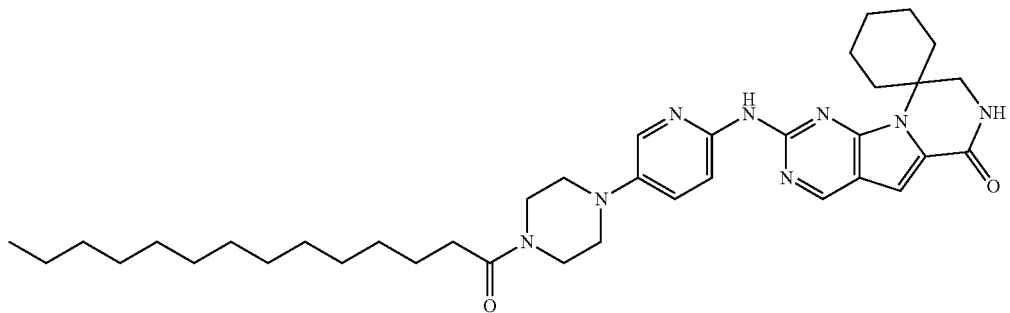 [SMILES: CCCCCCCCCCCCCC(=O)N1CCN(c2ccc(Nc3ncc4cc5n(c4n3)C3(CCCCC3)CNC5=O)nc2)CC1]

The compound shown below is another demonstrative embodiment of a substituted pyridinylpiperazine-pyrrolopyrimidine compound according to the present approach. In this embodiment, 'm' is 2 and 'n' is 14.

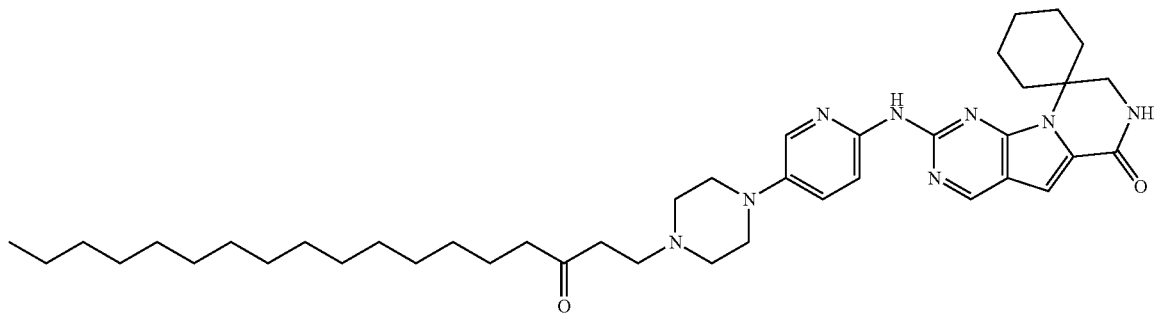 [SMILES: CCCCCCCCCCCCCCCC(=O)CCN1CCN(c2ccc(Nc3ncc4cc5n(c4n3)C3(CCCCC3)CNC5=O)nc2)CC1]

The compounds described herein, including salts thereof, may be used as a pharmaceutical compound for the treatment of cancer. The present approach also provides pharmaceutical formulations having a therapeutically effective amount of a compound, or a therapeutically acceptable salt(s) thereof, and a pharmaceutically acceptable carrier, diluent, or excipient therefor. All of these forms are within the present approach. It should be appreciated that a pharmaceutically acceptable carrier, as are known in the art, may be used.

Compounds described herein may be used in connection with methods of treating cancer, in a mammal, including humans, comprising administering to the mammal an amount of a substituted pyridinylpiperazine-pyrrolopyrimidine compound, or a pharmaceutically acceptable salt thereof, which is effective in treating such disorder or condition. For example, the present approach is useful for treating abnormal cell proliferation such a cancer. The compounds described herein may be used for treating the abnormal cell proliferation disorders, and in particular a cancer selected from the group consisting of cancers of the breast, ovary, cervix, prostate, testis, esophagus, stomach, skin, lung, bone, colon, pancreas, thyroid, biliary passages, buccal cavity and pharynx (oral), lip, tongue, mouth, pharynx, small intestine, colon-rectum, large intestine, rectum, brain and central nervous system, glioblastoma, neuroblastoma, keratoacanthoma, epidermoid carcinoma, large cell carcinoma, adenocarcinoma, adenocarcinoma, adenoma, adenocarcinoma, follicular carcinoma, undifferentiated carcinoma, papillary carcinoma, seminoma, melanoma, sarcoma, bladder carcinoma, liver carcinoma, kidney carcinoma, myeloid disorders, lymphoid disorders, Hodgkin's, hairy cells, and leukemia, by administering a therapeutically effective amount of a compound from the first class, the second class, or the third class, or a pharmaceutically acceptable salt thereof, to a subject having been diagnosed with such a cancer. In some embodiments, the present approach may be used in combination with, and/or to increase the effectiveness of, other therapies.

Embodiments of the present approach may be recognized by those having ordinary skill in the art, having reviewed the following detailed description.

DESCRIPTION

The following description includes the currently contemplated modes of carrying out exemplary embodiments of the present approach. The following description is not to be taken in a limiting sense, and is made merely for the purpose of illustrating the general principles of the invention.

Under the present approach, one or more substituted pyridinylpiperazine-pyrrolopyrimidine CDK 4/6 inhibitors may be used as anti-cancer therapeutics. According to the present approach, the pyridinylpiperazine portion is substituted with a fatty acid moiety, and preferably a fatty acid moiety having at least 14 carbons, and preferably between 14 carbons and about 22 carbons. The compounds described herein have useful pharmaceutical and medicinal properties. Many of the compounds exhibit significant selective CDK 4/6 inhibitory activity and therefore are of value in the treatment of a wide variety of clinical conditions in which CDK 4/6 kinases are abnormally elevated, or activated or present in normal amounts and activities, but where inhibition of the CDKs is desirable to treat a cellular proliferative disorder. In particular, these compounds are promising as anti-cancer therapeutics. Compounds in each class are described below the following definitions, which are applicable to embodiments of the present approach.

As used herein, the notation C(O) refers to a carbon to oxygen double bond. The term "halo" used herein means a halogen, and includes fluorine, chlorine, bromine, or iodine, bonded as is understood in the art.

The term "alkyl" used herein refers to saturated aliphatic groups, including straight-chain alkyl groups (e.g., methyl, ethyl, etc.), branched-chain alkyl groups (isopropyl, tert-butyl, etc.), cycloalkyl (alicyclic) groups (cyclopropyl, cyclopentyl, cyclohexyl, cycloheptyl, cyclooctyl), alkyl-substituted cycloalkyl groups, and cycloalkyl substituted alkyl groups. The term "alkyl" also includes alkenyl groups and alkynyl groups. General formula may use the term "Cn-alkyl", wherein n is an integer from, e.g., 1-20, to indicate a particular alkyl group (straight- or branched-chain) of a particular range or number of carbons in the group. For example, the term $C_1$-$C_3$-alkyl includes, but is not limited to, methyl, ethyl, propyl, and isopropyl. Similarly, the term $C_{3-6}$-cycloalkyl includes, but is not limited to, cyclopropyl, cyclopentyl, and cyclohexyl. Alkyl groups, as well as cycloalkyl groups, may be unsubstituted or substituted. Thus, the term alkyl includes both "unsubstituted alkyl" and "substituted alkyl", the latter of which refers to moieties having substituents replacing a hydrogen on one or more carbons of the hydrocarbon backbone.

The term "alkenyl" includes unsaturated aliphatic groups analogous in length and possible substitution to the alkyls described above, but which contain at least one double bond. Alkenyl also include "unsubstituted alkenyls" and "substituted alkenyls," the latter of which refers to moieties having substituents replacing a hydrogen on one or more carbons of the hydrocarbon backbone.

For example, the term "alkenyl" includes straight-chain alkenyl groups (e.g., ethenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups that include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$-$C_6$ for straight chain, $C_3$-$C_6$ for branched chain). Likewise, cycloalkenyl groups may have from 3-8 carbon atoms in their ring structure, and more preferably have 5 or 6 carbons in the ring structure. The term $C_2$-$C_6$ includes alkenyl groups containing 2 to 6 carbon atoms.

The term "alkynyl" includes unsaturated aliphatic groups analogous in length and possible substitution to the alkyls described above, but which contain at least one triple bond. Moreover, the term alkynyl includes both "unsubstituted alkynyls" and "substituted alkynyls," the latter of which refers to alkynyl moieties having substituents replacing a hydrogen on one or more carbons of the hydrocarbon backbone.

As examples, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups that include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$-$C_6$ for straight chain, $C_3$-$C_6$ for branched chain). The term $C_2$-$C_6$ includes alkynyl groups containing 2 to 6 carbon atoms.

The term "substituted" is intended to describe moieties having substituents replacing a hydrogen on one or more atoms, e.g. C, O or N, of a molecule. Such substituents can include, for example but not limited to, alkyl, alkoxy, alkenyl, alkynyl, halo, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, morpholino, phenol, benzyl, phenyl, piperizine, cyclopentane, cyclohexane, pyridine, 5H-tetrazole, triazole, piperidine, or an aromatic or heteroaromatic moiety, and combinations thereof. Substitutions on the pyridinylpiperazine portion include a fatty acid moiety, as described herein. The fatty acid moiety preferably has at least 14 carbon atoms, and preferably includes between 14 carbon atoms and about 22 carbon atoms.

The terms "amine" or "amino" should be refer to both a molecule, or a moiety or functional group, as generally understood in the art, and may be primary, secondary, or tertiary. The term "amine" or "amino" includes compounds where a nitrogen atom is covalently bonded to at least one carbon, hydrogen or heteroatom. The terms include, for example, but are not limited to, "alkylamino," "arylamino," "diarylamino," "alkylarylamino," "alkylaminoaryl," "arylaminoalkyl," "alkaminoalkyl," "amide," "amido," and "aminocarbonyl." The term "alkyl amino" comprises groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group which is bound to at least one alkyl group and at least one aryl group. The term "alkaminoalkyl" refers to an alkyl, alkenyl, or alkynyl group bound to a nitrogen atom which is also bound to an alkyl group.

The term "amide," "amido" or "aminocarbonyl" includes compounds or moieties which contain a nitrogen atom which is bound to the carbon of a carbonyl or a thiocarbonyl group. The term includes "alkaminocarbonyl" or "alkylaminocarbonyl" groups which include alkyl, alkenyl, aryl or alkynyl groups bound to an amino group bound to a carbonyl group. It includes arylaminocarbonyl and arylcarbonylamino groups which include aryl or heteroaryl moieties bound to an amino group which is bound to the carbon of a carbonyl or thiocarbonyl group. The terms "alkylaminocarbonyl," "alkenylaminocarbonyl," "alkynylaminocarbonyl," "arylaminocarbonyl," "alkylcarbonylamino," "alkenylcarbonylamino," "alkynylcarbonylamino," and "arylcarbonylamino" are included in term "amide." Amides also include urea groups (aminocarbonylamino) and carbamates (oxycarbonylamino).

The term "aryl" includes groups, including 5- and 6-membered single-ring aromatic groups that may include from zero to four heteroatoms, for example, phenyl, pyrrole, furan, thiophene, thiazole, isothiaozole, imidazole, triazole, tetrazole, pyrazole, oxazole, isoxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, anthryl, phenanthryl, naphthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics." The aromatic ring can be substituted at one or more ring positions with such substituents as described above, as for example, alkyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term heteroaryl, as used herein, represents a stable monocyclic or bicyclic ring of up to 7 atoms in each ring, wherein at least one ring is aromatic and contains from 1 to 4 heteroatoms selected from the group consisting of O, N and S. Heteroaryl groups within the scope of this definition include but are not limited to: acridinyl, carbazolyl, cinnolinyl, quinoxalinyl, pyrrazolyl, indolyl, benzotriazolyl, furanyl, thienyl, benzothienyl, benzofuranyl, quinolinyl, isoquinolinyl, oxazolyl, isoxazolyl, indolyl, pyrazinyl, pyridazinyl, pyridinyl, pyrimidinyl, pyrrolyl, tetrahydroquinoline. As with the definition of heterocycle below, "heteroaryl" is also understood to include the N-oxide derivative of any nitrogen-containing heteroaryl. In cases where the heteroaryl substituent is bicyclic and one ring is non-aromatic or contains no heteroatoms, it is understood that attachment is via the aromatic ring or via the heteroatom containing ring, respectively.

The term "heterocycle" or "heterocyclyl" as used herein is intended to mean a 5- to 10-membered aromatic or nonaromatic heterocycle containing from 1 to 4 heteroatoms selected from the group consisting of O, N and S, and includes bicyclic groups. "Heterocyclyl" therefore includes the above mentioned heteroaryls, as well as dihydro and tetrahydro analogs thereof. Further examples of "heterocyclyl" include, but are not limited to the following: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, oxetanyl, pyranyl, pyrazinyl, pyrazolyl, pyridazinyl, pyridopyridinyl, pyridazinyl, pyridyl, pyrimidyl, pyrrolyl, quinazolinyl, quinolyl, quinoxalinyl, tetrahydropyranyl, tetrazolyl, tetrazolopyridyl, thiadiazolyl, thiazolyl, thienyl, triazolyl, azetidinyl, 1,4-dioxanyl, hexahydroazepinyl, piperazinyl, piperidinyl, pyridin-2-onyl, pyrrolidinyl, morpholinyl, thiomorpholinyl, dihydrobenzoimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl, and N-oxides thereof. Attachment of a heterocyclyl substituent can occur via a carbon atom or via a heteroatom.

The term "acyl" includes compounds and moieties which contain the acyl radical (CH3CO—) or a carbonyl group. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups and may include cyclic groups such as cyclopentoxy. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "carbonyl" or "carboxy" includes compounds and moieties which contain a carbon connected with a double bond to an oxygen atom, and tautomeric forms thereof. Examples of moieties that contain a carbonyl include aldehydes, ketones, carboxylic acids such as fatty acid moieties, amides, esters, anhydrides, etc. The terms "fatty acid moiety," "carboxy moiety," and "carbonyl moiety" refer to groups such as "alkylcarbonyl" groups wherein an alkyl group is covalently bound to a carbonyl group, "alkenylcarbonyl" groups wherein an alkenyl group is covalently bound to a carbonyl group, "alkynylcarbonyl" groups wherein an alkynyl group is covalently bound to a carbonyl group, "arylcarbonyl" groups wherein an aryl group is covalently attached to the carbonyl group. Furthermore, the term also refers to groups wherein one or more heteroatoms are covalently bonded to the carbonyl moiety. For example, the term includes moieties such as, for example, aminocarbonyl moieties, (wherein a nitrogen atom is bound to the carbon of the carbonyl group, e.g., an amide), aminocarbonyloxy moieties, wherein an oxygen and a nitrogen atom are both bond to the carbon of the carbonyl group (e.g., also referred to as a "carbamate"). Furthermore, aminocarbonylamino groups (e.g., ureas) are also include as well as other combinations of carbonyl groups bound to heteroatoms (e.g., nitrogen, oxygen, sulfur, etc. as well as carbon atoms). Furthermore, the heteroatom can be further substituted with one or more alkyl, alkenyl, alkynyl, aryl, aralkyl, acyl, etc. moieties.

The term "thiocarbonyl" or "thiocarboxy" includes compounds and moieties which contain a carbon connected with a double bond to a sulfur atom. The term "thiocarbonyl moiety" includes moieties that are analogous to carbonyl moieties. For example, "thiocarbonyl" moieties include aminothiocarbonyl, wherein an amino group is bound to the carbon atom of the thiocarbonyl group, furthermore other thiocarbonyl moieties include, oxythiocarbonyls (oxygen bound to the carbon atom), aminothiocarbonylamino groups, etc.

The term "ether" includes compounds or moieties that contain an oxygen bonded to two different carbon atoms or heteroatoms. For example, the term includes "alkoxyalkyl" which refers to an alkyl, alkenyl, or alkynyl group covalently bonded to an oxygen atom that is covalently bonded to another alkyl group.

The term "ester" includes compounds and moieties that contain a carbon or a heteroatom bound to an oxygen atom that is bonded to the carbon of a carbonyl group. The term "ester" includes alkoxycarboxy groups such as methoxycarbonyl, ethoxycarbonyl, propoxycarbonyl, butoxycarbonyl, pentoxycarbonyl, etc. The alkyl, alkenyl, or alkynyl groups are as defined above.

The term "thioether" includes compounds and moieties which contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom that is bonded to an alkyl group. Similarly, the term "alkthioalkenyls" and alkthioalkynyls" refer to compounds or moieties wherein an alkyl, alkenyl, or alkynyl group is bonded to a sulfur atom which is covalently bonded to an alkynyl group.

The term "hydroxy" or "hydroxyl" includes groups with an —OH or —O—.

The terms "polycyclyl" or "polycyclic radical" include moieties with two or more rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, aralkylaminocarbonyl, alkenylaminocarbonyl, alkylcarbonyl, arylcarbonyl, aralkylcarbonyl, alkenylcarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

Additionally, the phrase "any combination thereof" implies that any number of the listed functional groups and molecules may be combined to create a larger molecular architecture. For example, the terms "phenyl," "carbonyl" (or "=O"), "—O—," "—OH," and $C_{1-6}$ (i.e., —CH$_3$ and —CH$_2$CH$_2$CH$_2$—) can be combined to form a 3-methoxy-4-propoxybenzoic acid substituent. It is to be understood that when combining functional groups and molecules to create a larger molecular architecture, hydrogens can be removed or added, as required to satisfy the valence of each atom.

The compounds described herein include bonds between adjacent atoms and/or hydrogens as required to satisfy the valence of each atom, as would be understand by those having an ordinary level of skill in the art. Bonds and/or hydrogen atoms are added, if necessary, to provide the following number of total bonds to each of the following types of atoms: carbon: four bonds; nitrogen: three bonds; oxygen: two bonds; and sulfur: two-six bonds.

The phrase "pharmaceutically effective amount" as used herein indicates an amount necessary to administer to a host, or to a cell, tissue, or organ of a host, to achieve a therapeutic result, such as the regulating, modulating, or inhibiting protein kinase activity, e.g., inhibition of the activity of a protein kinase, or treatment of cancer. A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

The terms "treat," "treated," "treating," and "treatment" include the diminishment or alleviation of at least one symptom associated or caused by the state, disorder or disease being treated, in particular, cancer. In certain embodiments, the treatment comprises diminishing and/or alleviating at least one symptom associated with or caused by the cancer being treated, by the compound of the invention. For example, treatment can be diminishment of one or several symptoms of a cancer or complete eradication of a cancer.

The compounds described herein include what this disclosure refers to as a fatty acid moiety, also known as a carbonyl moiety. As used herein, a fatty acid is a carboxylic acid with an aliphatic chain, which may be saturated or unsaturated, although saturated chains are preferred. Examples of saturated fatty acids include lauric acid ($CH_3(CH_2)_{10}C(O)OH$), palmitic acid ($CH_3(CH_2)_{14}C(O)OH$), stearic acid ($CH_3(CH_2)_{16}C(O)OH$), and myristic acid ($CH_3(CH_2)_{12}C(O)OH$). Oleic acid ($CH_3(CH_2)_7CH=CH(CH_2)_7C(O)OH$) is an example of a naturally occurring unsaturated fatty acid. References may also be made to the salt or ester of a fatty acid, as well as its fatty amide moiety, but for simplicity these are included in the meaning of fatty acid moiety as used herein. For example, myristic acid may be referred to as myristate, and oleic acid may be referred to as oleate. A fatty acid moiety may also be a carboacyl of the fatty acid, i.e., a group formed by the loss of a hydroxide group of a carboxylic acid. In some embodiments, a fatty acid moiety may be bonded to a therapeutic agent through an amide bond. As an example, a myristic acid conjugate may have a fatty acid moiety $CH_3(CH_2)_{12}CO-NH-$, where the tertiary nitrogen is bonded to the therapeutic agent:

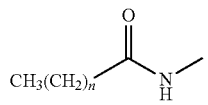

and n is an integer from 1 to 20, and is preferably 10 to 20. This may result when the myristate moiety is conjugated through myristoylation, resulting in a tetradecanamide (or myristamide) group.

Under the present approach, anti-cancer CDK 4/6 inhibitors comprise substituted pyridinylpiperazine-pyrrolopyrimidine compounds as shown below in general formula [1].

[1]

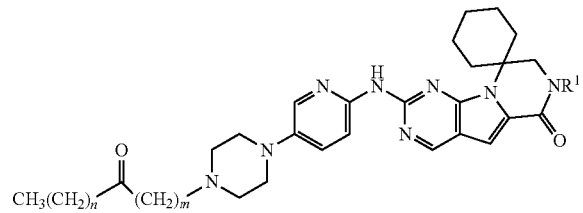

As used in generic formula [1], 'm' in the fatty acid moiety is an integer from 0-4, and more preferably 0-2, such that when m is 0 there is a direct bond to the nitrogen in the piperazine; and 'n' in the fatty acid moiety represents an integer from 13 to 22, and is preferably from 14 to 20, and may be 14, 15, 16, 17, 18, 19, 20, 21, or 22; and preferably is a saturated straight chain;

$R^1$ is selected from the group consisting of hydrogen, $C_1$-$C_8$-alkyl, substituted $C_1$-$C_8$-alkyl, $C_3$-$C_8$-cycloalkyl, substituted $C_3$-$C_8$-cycloalkyl, aryl, substituted aryl, heteroaryl and substituted heteroaryl. halo-substituted alkoxy group In one preferred embodiment of the present approach, the anti-cancer CDK 4/6 inhibitor has the chemical formula [2] shown below. In such embodiments, 'm' is 0, 'n' is 12, resulting in the fatty acid moiety comprising a myristate moiety, and $R^1$ is hydrogen. This embodiment resembles Trilaciclib, a CDK 4/6 inhibitor currently in phase 2 clinical trials, for use to reduce side effects associated with chemotherapy. However, formula [2] includes a myristate moiety on the pyridinylpiperazine. It should be appreciate that $R_1$ in formula 2 is H, but as described herein may be $C_1$-$C_8$-alkyl, substituted $C_1$-$C_8$-alkyl such as a halo-alkyl, $C_3$-$C_8$-cycloalkyl, substituted $C_3$-$C_8$-cycloalkyl, aryl, substituted aryl, heteroaryl and substituted heteroaryl.

[2]

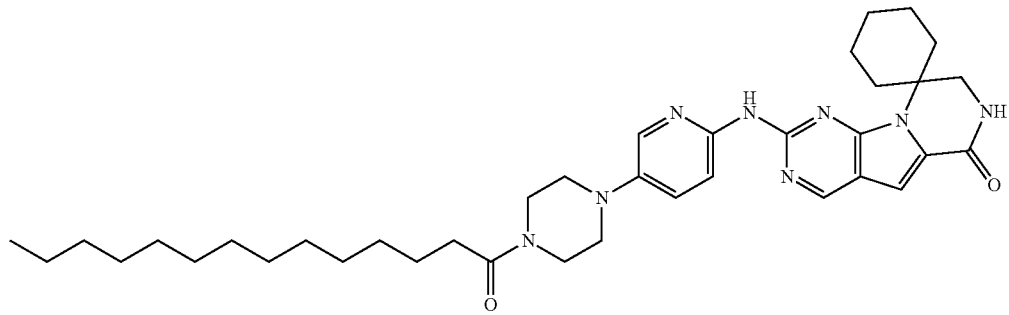

Embodiments of the present approach, including the embodiment having the structure shown in formula [2] above, and formula [3] below, include what this disclosure references as a fatty acid substituted at the pyridinylpiperazine. The fatty acid moiety, particularly at this location on the structure, significantly improves the cellular uptake of the compound, greatly increasing its inhibition of cancer stem cell proliferation, among having other beneficial effects. As a result, compounds according to the present approach inhibit growth in vitro of lung cancer cell lines. And may be useful as chemoprotective agents through their ability to inhibit cell cycle progression of normal untransformed cells, as well as for treating cancer, reducing a cancer's resistance to treatment, preventing metastatic disease, preventing tumor recurrence, preventing at least one of radiation therapy resistance, chemotherapy resistance and hormone therapy resistance, and/or preventing or reducing the proliferation of at least one of cancer cells, cancer stem cells, and circulating tumor cells.

Methods of treatment described herein are preferably carried out by administering a therapeutically effective amount of a compound from either the first class or the second class, to a subject in need of treatment. The compounds are readily synthesized and can be administered by a variety of routes, including orally and parenterally, and have little or no toxicity.

Compounds according to the present approach may be synthesized starting with Trilaciclib, which is commercially available. Alternatively, synthesis options are publicly available, including, for example, the synthesis schemes disclosed in U.S. Pat. No. 8,598,197, which is incorporated herein by reference in its entirety. Starting with Trilaciclib, the methylpiperazine may be de-methylated using methods known in the art. Following de-methylation, myristoylation may be used to form the compound.

As another example, the following synthesis method may be used for embodiments having a myristate moiety. Myristic acid may be converted to myristoyl chloride, and reacted

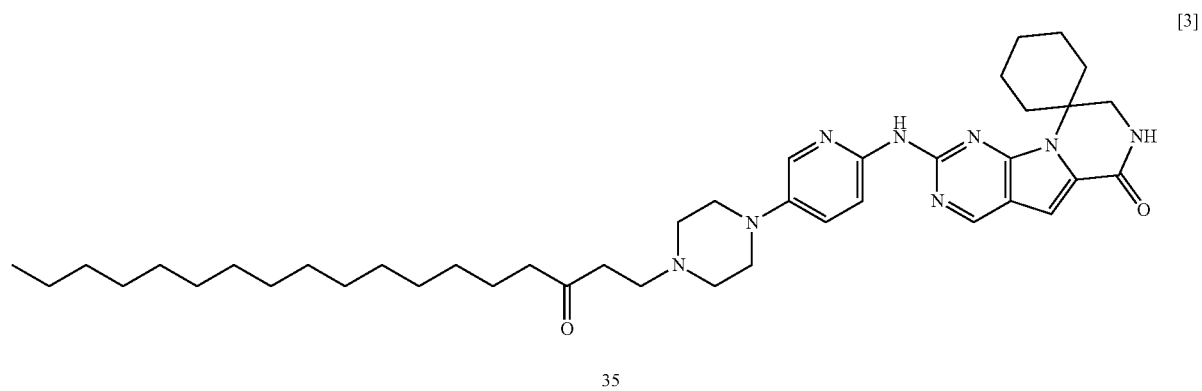

[3]

A second demonstrative embodiment is shown above as formula [3], in which $R^1$ is hydrogen, m is 2, and n is 14. As a result, this embodiment has a 14-carbon, saturated fatty acid (i.e., palmitate) moiety. The compound shown in formulas [2] and [3] have remarkably improved inhibition of MCF7 cells in the mammosphere assay, compared to Trilaciclib. It should be appreciated that similar results are expected for other fatty acid moieties having as few as 11 carbons, preferably at least 14 carbons, and as many as 22 carbons.

The present approach describes pharmaceutical compositions comprising a therapeutically effective amount of a compound from the first class or the second class, or a pharmaceutically acceptable salt thereof, and a pharmaceutically acceptable carrier, diluent, or excipient therefor. Compounds according to the present approach may be used as anti-cancer therapeutics. Pharmaceutically-effective amounts of a compound in a pharmaceutically-acceptable carrier may be administered to a subject according to means known in the art. In some embodiments, a compound of the present approach may be used in conjunction with other cancer therapies, such as but not limited to chemotherapeutics, mitochondrial biogenesis inhibitors (e.g., mitoribosins, mitoketoscins, repurposcins such as antimitoscins), radiation therapy, phototherapy, and caloric restriction.

The selective inhibition of CDK 4/6 also indicates that the compounds described herein may be used to reduce or eliminate drug and/or therapy resistance in cancers. Because of their inhibitory activity against CDKs and other kinases, the compounds of the present approach are also useful research tools for studying the mechanism of action for such kinases, and may be used both in vitro and in vivo.

with 2-methyl-2-propanyl 1-piperazinecarboxylate (shown below as 1-BOC-piperazine), in the presence of 4-methylmorpholine (NMM) and Dichloromethane (DCM), as shown below.

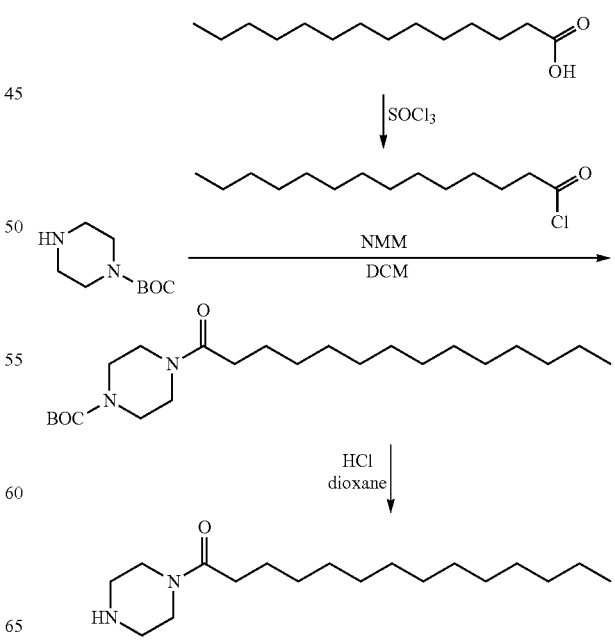

The intermediate product may be reacted with HCl and dioxane to form 1-(1-Piperazinyl)-1-tetradecanone. The method continues as shown below. It should be appreciated that DiPEA is Hünig's base (N, N-diisopropylethylamine), DMA is dimethylacetamide, and THF is tetrahydrofuran. It should also be appreciated that the fatty acid moiety may be modified in the initial step above, using the desired alkyl.

include the plural forms as well, unless the context clearly indicates otherwise. The present approach encompasses numerous alternatives, modifications, and equivalents as will become apparent from consideration of the following detailed description.

It will be understood that although the terms "first," "second," "third," "a)," "b)," and "c)," etc. may be used

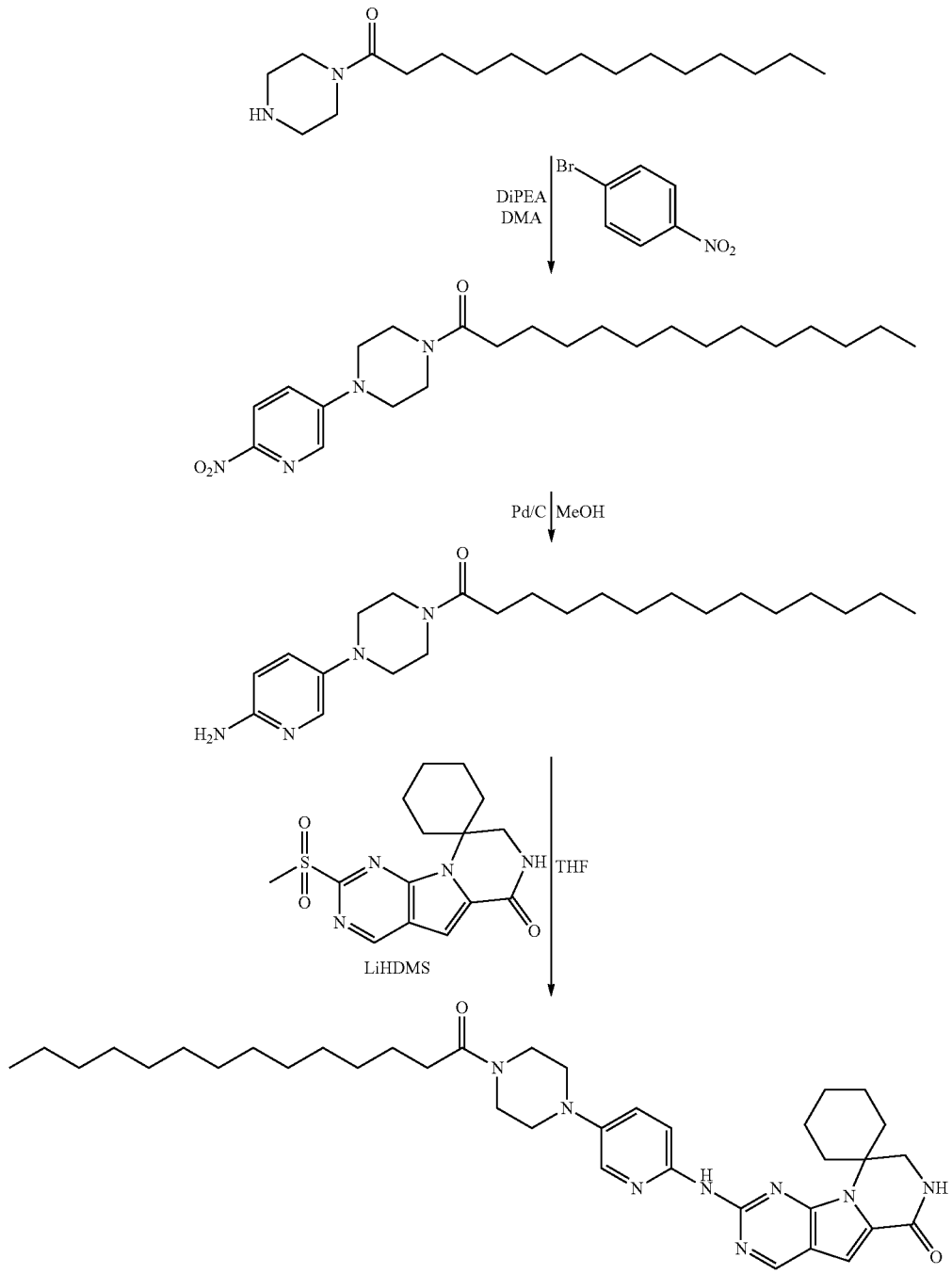

The terminology used in the description of embodiments of the present approach is for the purpose of describing particular embodiments only and is not intended to be limiting. As used in the description and the appended claims, the singular forms "a," "an" and "the" are intended to herein to describe various elements of the present approach, and the claims should not be limited by these terms. These terms are only used to distinguish one element of the present approach from another. Thus, a first element discussed below could be termed an element aspect, and similarly, a third without departing from the teachings of the present approach. Thus, the terms "first," "second," "third," "a)," "b)," and "c)," etc. are not intended to necessarily convey a sequence or other hierarchy to the associated elements but are used for identification purposes only. The sequence of operations (or steps) is not limited to the order presented in the claims.

Unless otherwise defined, all terms (including technical and scientific terms) used herein have the same meaning as commonly understood by one of ordinary skill in the art. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. All publications, patent applications, patents and other references mentioned herein are incorporated by reference in their entirety. In case of a conflict in terminology, the present specification is controlling.

Also, as used herein, "and/or" refers to and encompasses any and all possible combinations of one or more of the associated listed items, as well as the lack of combinations when interpreted in the alternative ("or").

Unless the context indicates otherwise, it is specifically intended that the various features of the present approach described herein can be used in any combination. Moreover, the present approach also contemplates that in some embodiments, any feature or combination of features described with respect to demonstrative embodiments can be excluded or omitted.

As used herein, the transitional phrase "consisting essentially of" (and grammatical variants) is to be interpreted as encompassing the recited materials or steps "and those that do not materially affect the basic and novel characteristic(s)" of the claim. Thus, the term "consisting essentially of" as used herein should not be interpreted as equivalent to "comprising."

The term "about," as used herein when referring to a measurable value, such as, for example, an amount or concentration and the like, is meant to encompass variations of ±20%, ±10%, ±5%, 1%, ±0.5%, or even ±0.1% of the specified amount. A range provided herein for a measurable value may include any other range and/or individual value therein.

Having thus described certain embodiments of the present approach, it is to be understood that the scope of the appended claims is not to be limited by particular details set forth in the above description as many apparent variations thereof are possible without departing from the spirit or scope thereof as hereinafter claimed.

What is claimed is:

1. A compound comprising the general formula

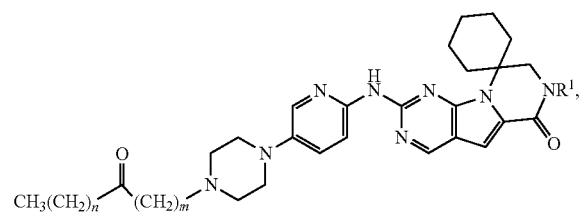

in which:
'm' is an integer from 0-4, 'n' is an integer from 13 to 22, and $R^1$ is selected from the group consisting of hydrogen, C1-C8-alkyl, substituted C1-C8-alkyl, C3-C8-cycloalkyl, substituted C3-C8-cycloalkyl, aryl, substituted aryl, heteroaryl and substituted heteroaryl.

2. The compound of claim 1, wherein 'm' is an integer from 0-2, and 'n' is an integer from 14 to 20.

3. The compound of claim 2, wherein $R^1$ is one of H, C1-C8-alkyl, and substituted C1-C8-alkyl.

4. The compound of claim 1, in which m is 0, n is 12, and $R^1$ is hydrogen.

5. A pharmaceutical composition comprising a compound of claim 1, and a pharmaceutically acceptable carrier.

* * * * *